United States Patent [19]

Krauter

[11] Patent Number: 5,019,121
[45] Date of Patent: May 28, 1991

[54] HELICAL FLUID-ACTUATED TORSIONAL MOTOR

[75] Inventor: Allan I. Krauter, Syracuse, N.Y.

[73] Assignee: Welch Allyn, Inc., Skaneateles Falls, N.Y.

[21] Appl. No.: 528,432

[22] Filed: May 25, 1990

[51] Int. Cl.⁵ .................. A61B 1/00; F01B 19/00; F16J 3/00
[52] U.S. Cl. .................................. 128/4; 92/48; 92/61; 92/92; 92/117 R; 92/118; 92/94
[58] Field of Search .................. 128/4, 6; 358/98; 92/48, 61, 54, 117 R, 118, 89, 90, 91, 92, 94

[56] References Cited

U.S. PATENT DOCUMENTS

| | | |
|---|---|---|
| 2,386,610 | 10/1945 | Hunter ........................ 92/92 |
| 3,066,853 | 12/1962 | Landenberger ............... 92/90 |
| 3,276,477 | 10/1966 | Bleasdale ..................... 92/93 |
| 3,315,606 | 4/1967 | Piros ........................... 92/48 |
| 3,490,733 | 1/1970 | Berthaud ..................... 92/92 |
| 3,924,519 | 12/1975 | England ....................... 92/92 |
| 4,108,050 | 8/1978 | Paynter ........................ 92/48 |
| 4,616,556 | 10/1986 | Meilman et al. .............. 92/92 |
| 4,792,173 | 12/1988 | Wilson ......................... 92/92 |
| 4,794,912 | 1/1989 | Lia .............................. 92/92 |

FOREIGN PATENT DOCUMENTS

| | | | |
|---|---|---|---|
| 0225834 | 7/1962 | Australia ................... 92/90 |
| 1022755 | 3/1953 | France ..................... 92/92 |
| 0144088 | 1/1962 | U.S.S.R. ................... 92/92 |
| 0937801 | 6/1982 | U.S.S.R. ................... 92/89 |

OTHER PUBLICATIONS

*IBM Technical Disclosure Bulletin* vol. 8, No. 6, 11/65, 1 Sheet.

Primary Examiner—Edward K. Look
Assistant Examiner—Thomas Denion
Attorney, Agent, or Firm—Wall and Roehrig

[57] ABSTRACT

A hydraulically or pneumatically actuated fluid-dynamic motor has an elongated elastomeric bladder, a braid disposed over the bladder, and a flexible but substantially incompressible spine disposed between the braid and the bladder. The muscle or motor is configured in a helix with the spine arranged on the inside of the helix. Application of fluid under pressure to the bladder causes one end of the helical motor to untwist or rotate relative to the other end. Upon deflation of the bladder, the spine causes the bladder to deflate and rotate the other end in the opposite direction. This fluid dynamic motor provides an azimuthal motion that can be employed for the steering section of an elongated flexible probe, such as a borescope or endoscope.

12 Claims, 1 Drawing Sheet

U.S. Patent
May 28, 1991
5,019,121
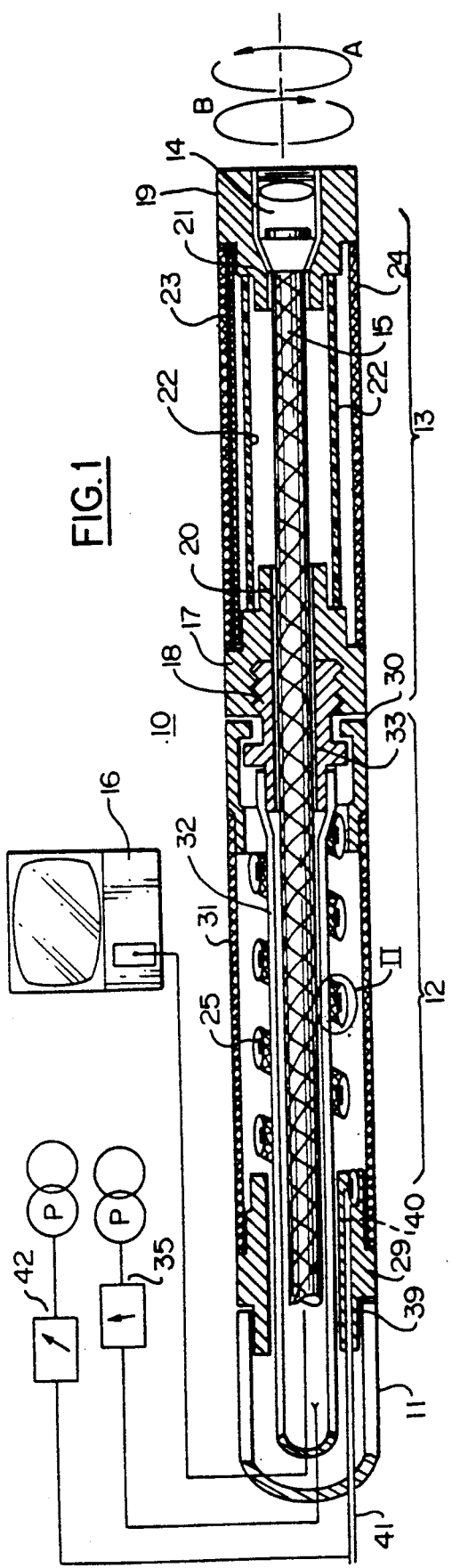
FIG. 1
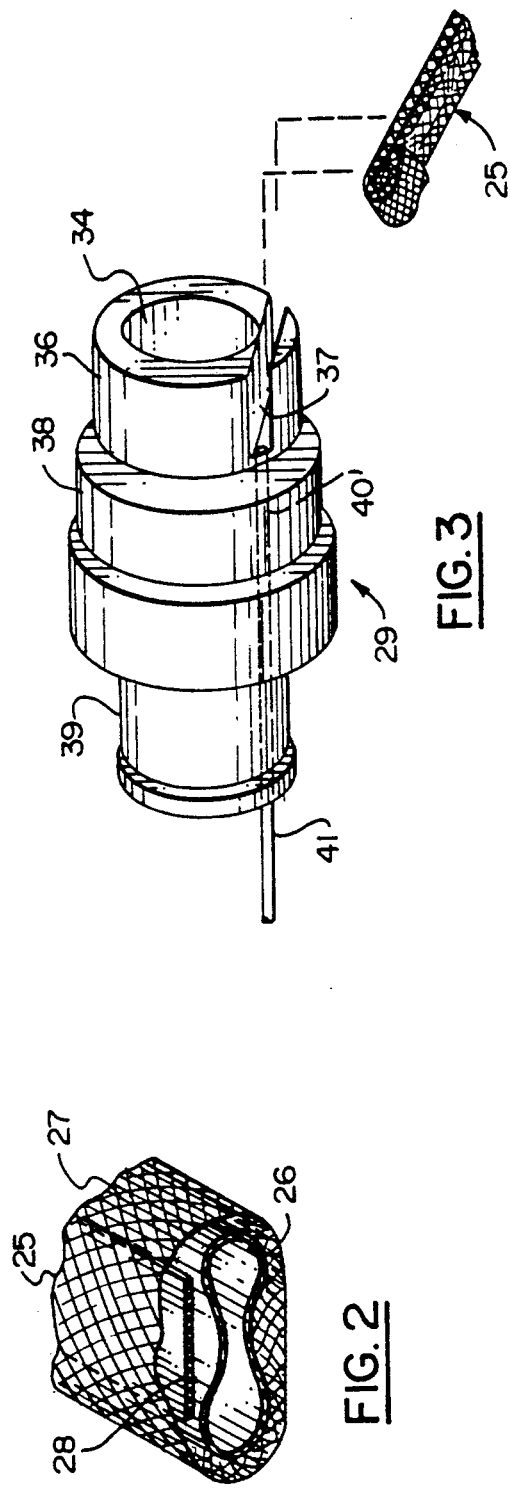
FIG. 2
FIG. 3

HELICAL FLUID-ACTUATED TORSIONAL MOTOR

BACKGROUND OF THE INVENTION

This invention relates to hydraulically or pneumatically actuated motors, and is more particularly directed to a torsional fluid-dynamic muscle which can be made of small diameter and incorporated into a steering or articulation section of a flexible elongated probe. The invention is also directed to improvements in borescopes and/or endoscopes which permit four-way steering of the distal end of an insertion tube without reliance on the conventional, but delicate and trouble-prone cable-type steering movement. Additionally, the torsional fluid-dynamic muscle or motor of this invention has other applications including rotary actuators and gauges, grabbers, and supports for remote tools. The invention can also be regarded as a pump for converting an angular or torsional force to a fluid pressure.

Borescopes or similar flexible probes are generally configured as an elongated flexible insertion tube with a viewing head at its distal or forward end and a control housing for controlling or steering the distal or forward end. The typical borescope has a bendable tubular steering section or articulation section at the distal end adjacent the viewing head. The steering section comprises a series of alternating wobble washers and spacers, with control cables that extend through the wobble washers and then through the remainder of the flexible insertion tube. The steering cables connect with a steering control unit in the control section. Each such pair of cables is differentially displaced to bend the steering section. The viewing head can be remotely oriented to facilitate inspection of an object. Borescopes are often required to bend in narrow, tortuous passageways, so the diameter of the borescope is often quite limited, e.g. 6 mm. Also, the pathway to the object or target can be quite long, which then requires the insertion tube and the steering cables to be rather long, e.g. fifteen meters or more.

A number of cable-actuated articulation or steering mechanisms are known, and typical ones are discussed in U.S. Pat. Nos. 3,610,231; 3,739,770; 3,583,393; 3,669,098; 3,779,151; and 4,347,837. Another steering mechanism is described in U.S. Pat. No. 4,700,693.

These cable-actuated articulation mechanisms require the cables to have a significant amount of slack or play because bends and coils in the insertion tube effectively shorten the cables and because the articulation section bends at discrete points rather than following a smooth arc. However, in many applications the articulation section must be bent rather precisely to penetrate the tortuous passages into the area to be inspected without damaging delicate engine parts. For these reasons, cable tension must be limited and cable slack must be minimized. However, where the insertion tube is long, extra cable slack is often included to accommodate the increased cable tightening due to the substantial coiling and bending of the insertion tube through which the steering cables pass. A proposed arrangement to permit steering cables to be kept short as possible is described in U.S. Pat. No. 4,794,912. That patent describes a "muscle," i.e. a linear traction motor, that addresses many of the problems found in these prior-art steering mechanisms. Specifically, fluid dynamic muscles mounted adjacent the distal end of the insertion tube are actuated by pneumatic or hydraulic pressure supplied through small flexible tubes within the borescope insertion tube. Short steering cables connect the respective muscles with the articulation mechanism. As fluid pressure is applied differentially to a pair of muscles, the cables move differentially and the articulation mechanism bends the steering section a desired amount.

While this system avoids many of the above-mentioned problems, especially those associated with extremely long cables, there are remaining problems because of the reliance on an otherwise conventional cable steering mechanism. The steering section is rather complex and expensive, and does not follow a natural arc, as mentioned before. Further simplification, by replacing the cable drive steering mechanism, would be required to reduce or eliminate these residual drawbacks.

A hydraulic or pneumatic bending neck is proposed in copending and commonly-assigned U.S. patent application Ser. No. 538,232, filed June 18, 1990. In that arrangement, an articulation or steering mechanism is formed of an elongated fluid-controlled muscle that has a flexible spine arranged in the axial direction along one side and disposed in the interface between the bladder and the braid. The braid confines the bladder such that when the bladder is inflated, the bladder and braid expand laterally, but shorten axially. Because of the spine, the braid can shorten only on the side away from the spine, so the spine defines a bending plane for the bending neck. Preferably, the spine is arcuately biased in one direction so that when no pressure is applied the bending neck is bent in one direction in the bending plane. At full pressure the bending neck is bent in the opposite direction, and at an intermediate pressure, the bending neck is held straight.

This type of arrangement is capable of two-directional steering, i.e., bending that is confined to a single bending plane. It would be desirable to have four-way steering with fluid-dynamic bending, but as aforesaid, the bending neck is difficult to adapt for deflection in orthogonal directions.

OBJECTS AND SUMMARY OF THE INVENTION

It is an object of this invention to provide a simple, reliable steering mechanism which can be employed on an elongated flexible probe of small diameter.

It is another object of this invention to eliminate cables, wobble washers, and other complex mechanical actuation devices from the steering section for a probe.

According to an aspect of this invention a helical biased torsional fluid dynamic muscle or motor is constructed which is suited to provide a rotational or torsional direction of steering to a bending section of a borescope or similar probe. The fluid dynamic muscle has an elongated tubular elastomeric bladder in the form of a helix, a tubular braid disposed over the bladder in the helix, and a resiliently flexible but substantially incompressible helical spine that is situated between the bladder and the braid on the inner side of the helix. The bladder is sealed at its ends and the braid is attached at one end to an anchor member and at the other end to a swivel member. A pressure inlet through one end of the bladder permits fluid communication between a controlled fluid pressure source and the interior of the bladder. When pressure is applied, the fluid expands the bladder laterally, i.e., radially.

The braid constrains the bladder so that as it expands laterally, it shortens in its lengthwise, i.e. helical, direction. The spine restrains helical motion on the inside of the helix, so the braid shortens on the outside of the helix. This serves to rotate the swivel member in one direction by an angle that depends on the amount of pressure applied to the muscle. When the pressure is relieved, the spine acts on the bladder and braid so that fluid is expelled from the bladder. This lengthens the bladder on the outside of the helix, and causes the muscle to rotate the swivel member in the opposite direction. The spine can be in the form of a helical leaf or ribbon. The swivel member can serve as a connector or mount on which a fluid dynamic bending neck is affixed.

A signal and/or optical conduit can pass axially through the system from a video or optical viewing head at the distal tip. The conduit can be contained in a tubular core that passe from the swivel, proximally within the helix and out through a passage in the anchor member.

The above and other objects, features, and advantages of this invention will be more fully appreciated from the ensuing description of a preferred embodiment which is to be read in conjunction with the accompanying Drawing:

BRIEF DESCRIPTION OF THE DRAWING

FIG. 1 is a schematic sectional view of an elongated flexible probe that incorporates a torsional fluid dynamic helical muscle or motor according to one embodiment of this invention.

FIG. 2 is an enlargement of a portion of FIG. 1.

FIG. 3 is an assembly view of a portion of the embodiment of FIG. 1.

DETAILED DESCRIPTION OF THE PREFERRED EMBODIMENT

With reference to the Drawing, and initially to FIG. 1, a flexible video probe 10 has an elongated flexible insertion tube 11, of which only a distal portion is shown, an azimuthal steering section 12 situated at the distal end of the insertion tube, and a bending section 13 situated at the distal end of the azimuthal steering section 12. At the distal end of the bending section 13 there is a video head 14. A conduit 15 that contains signal and control conductors and a fiber optic bundle for illumination extends axially within the insertion tube 11 and through the sections 12 and 13 to connect the video head 14 with a video processor unit 16.

The bending section 13 is capable of two-way bending in a bending plane that is up to 60 to 90 degrees either side of a straight orientation.

In this arrangement, as shown, the bending neck 13 is arranged as generally as described in the copending patent application Ser. No. 539,232 having a common assignee. There is a proximal connector 17 that is screwed onto a threaded swivel member 18 at the distal end of the azimuthal steering section 12. A distal end piece 19 at the distal end of the bending section 13 mounts the video viewing head 14. A passage 20 extends axially through the proximal connector 17 and a passage 21 extends through the distal end piece 19; these passages 20, 21 carry the conduit 15. In the bending section 13, an elongated elastomeric bladder 22 is coupled to the connector 17 and end piece 19, and a flexible but incompressible spine 23 is situated on one side of the bladder and extends between the connector 17 and the end piece 19. A braid 24 that is formed of right hand and left hand helically wound filaments is disposed over the bladder 22 and spine 23 and is mechanically connected to the connector 17 and the end piece 19. The bending section 13 operates in a manner that is generally described in copending patent application Ser. No. 539,232.

The azimuthal steering section 12 has a helical biased muscle or motor 25 that is driven to rotate in the azimuthal direction by controlled fluid pressure (either pneumatic or hydraulic). This muscle 25 is formed of a helical elongated elastomeric bladder that is covered with a generally helical braid 20. A helical spine 28, which is formed of a ribbon of a flexible, but generally incompressible material such as a suitable spring metal alloy, is situated between the bladder 26 and the braid 27, but on the inside of the helix. The construction of the braid 27 and bladder 26 can be generally as shown in FIG. 2. The helix should have a suitable number of turns, and, although only about four turns are shown in FIG. 1, the helically biased muscle 25 could be configured of twelve or more turns.

A proximal connector 29 fits into the distal end of the insertion tube 11, while a distal end bushing 30 holds the swivel member 18 to permit rotation thereof. A sheath or skin 31 of a suitable material covers the azimuthal steering section 12 and extends between the connector 29 and the bushing 30. A tubular core 32 extends proximally from a protuberance 33 on the swivel member 18 and passes within the helix of the muscle 25 and through a central passage 34 in the proximal connector 29 and then continues axially within the insertion tube 11. A controllable pressure source 35 supplies pressurized fluid through the tubular core 32 to the interior of the bladder 22 of the bending section 13. The degree of arcuate bending of the section 13 depends on the pressure that is applied from this source 35.

As shown in FIG. 3, the proximal connector 29 has a first annular region 36 in which there is cut a slot 37 to receive a proximal end of the helical muscle 25. Favorably, the elongated braid 27 and bladder 26 are folded over at the end and inserted into the slot 37. Then the slot is potted in epoxy or other potting compound. The region 36 provides a surface from which the first turn of the helix starts. A second annular region 38 receives the proximal end of the flexible sheath 31. A proximal-side protuberance 39 fits into the distal end of the insertion tube 11.

An axial fluid passage 40 is bored through the connector 29 into the slot 37 in which the end of the helical muscle 25 is affixed. An opening is bored through this hole into the potting and the proximal end of the muscle 25 to provide fluid communication with the interior of the bladder 26. As shown in FIG. 1, a fluid conduit 41 extends proximally from the fluid passage 40 and extends within the insertion tube 11 to a controllable pressure source 42. The pressure source 42 provides pneumatic or hydraulic pressure at a selected level to control a degree of rotation of the swivel 18 and thus the bending plane of the bending section 13. This degree of rotation should be arranged to be 180° or greater. The spine 28 is on the inside of the spiral in the helical muscle 25. When pressure is applied from the source 42 to inflate the bladder 26, the bladder expands radially, i.e., laterally. The filaments of the braid 27 constrain this expansion so that the braid 27 will tend to shorten i.e. in the direction of the helix. The spine 28 prevents the inside of the muscle from contracting, so that the outside of the helix shortens differentially. Inflation tends to unwind the helical spine which, in this case, rotates the swivel 18 and the attached bending neck 13 in the direction of arrow A. When pressure is relieved from the bladder 26, the muscle 25 relaxes and elongates helically on the outside, thereby allowing the spine to rewind, which rotates the swivel 18 and the bending neck 13 in the direction of arrow B. Preferably, the bending neck 13 should be capable of rotating 90° or more on either side of the zero position. This zero position occurs at a pressure approximately halfway between zero gauge pressure and the maximum allowable gauge pressure.

The arrangement as shown and described here can be configured for either pneumatic or hydraulic operation. In the case of a pneumatic device, a portable unit can be constructed which is controlled by a small cylinder of compressed gas.

Also in this embodiment, the helical torsional motor 25 is wound as a right-hand helix, but in other embodiments, the motor could be configured as a left-hand helix. The left hand configuration would produce rotation in the direction of arrow B during inflation and rotation in the direction of arrow A when pressure is relieved. Moreover, in some applications, a pair of oppositely wound helices could be employed, and differentially controlled for precise azimuthal steering. Also, in alternative embodiments, the spine can be outside the braid, and bonded to it at the ends and one or more intermediate points.

A rotational seal can be employed between the swivel 18 and the bushing 30. This permits the insertion tube 11 to serve as a conduit for air between the controlled pressure source 42 and the azimuthal steering section 12. In that case, the fluid conduit 41 could be eliminated or could terminate a short distance proximally of the connector 29.

While this invention has been described in detail with reference to one preferred embodiment, it should be understood that the invention is not limited to that precise embodiment. Rather, many modifications and variations will present themselves to those of skill in the art without departing from the scope and spirit of this invention, as defined in the appended claims.

What is claimed is:

1. A helical biased torsional fluid dynamic motor which comprises
    an elongated elastomeric bladder in the form of a helix;
    a tubular braid disposed over said bladder in said helix;
    a helical spine that is resiliently flexible but is substantially inextensible and incompressible along the helix direction and disposed outside said bladder and adjacent said braid on the inner side of the helix;
    means sealing said bladder at its ends;
    means to communicate fluid pressure between a controlled fluid pressure source and the inside of said bladder to permit controlled inflation and deflation of said bladder;
    anchor means at one of distal and proximal ends of said braid to which said one end is affixed,
    swivel means at the other end of said braid to which said other end is affixed;
    said fluid dynamic motor being operative such that when pressure is applied to said bladder the fluid expands the bladder radially but shortens the braid helically on the outside of the helix causing said swivel means to rotate in one direction, and when said pressure is relieved said spine acts to deflate said bladder and lengthen said braid on the outside of the helix causing said swivel means to rotate in the opposite direction.

2. A helical biased torsional fluid dynamic motor according to claim 1 further comprising a tubular core extending axially within said helix and being attached to one of said swivel means and said anchor means.

3. A helical biased torsional fluid dynamic motor according to claim 1 wherein said spine is in the form of a helical ribbon.

4. A helical biased torsional fluid dynamic motor according to claim 1 wherein said swivel means includes an outer bushing and an inner swivel portion that is freely rotatable in said outer bushing, and said swivel portion includes a receptacle onto which said braid other end is affixed.

5. A helical biased torsional fluid dynamic motor according to claim 1 wherein said spine is disposed between said bladder and said braid.

6. An elongated flexible probe which comprises an elongated flexible insertion tube having a distal end, a helical biased torsional fluid dynamic motor disposed at the distal end of said insertion tube said motor including
    an anchor attached onto said distal end of said insertion tube,
    an elongated tubular elastomeric bladder in the form of a helix and having means sealing the ends thereof to define an interior thereof;
    a tubular braid disposed over said bladder and in the form of said helix, with a proximal end of the braid secured to said anchor;
    a helical spine that is resiliently flexible but is substantially incompressible along its helical direction, and disposed outside said bladder and adjacent said braid on a radially inward side of the helix;
    swivel means disposed at a distal end of the braid and onto a portion of which said distal end of the braid is affixed;
    said anchor including fluid conduit means extending through said insertion tube end communicating between a controlled fluid pressure source and the interior of said bladder, to permit controlled inflation and deflation of said bladder, such that when fluid pressure is applied to inflate said bladder, the fluid expands the bladder radially but shortens the braid helically on the outside of the helix thus causing said swivel to rotate in one direction, and such that when said pressure is relieved to deflate said bladder said spine acts to deflate said bladder and lengthens said braid on the outside of the helix thus causing said swivel means to rotate in the opposite direction; and
    a tubular fluid-controlled biased bending neck supported on said swivel means and including means communicating with a second controlled fluid pressure source such that when pressure is applied from said second source to said bending neck the latter bends in one direction in a bending plane and when such pressure is relieved the bending neck bends in an opposite direction in said bending plane.

7. The elongated flexible probe of claim 6 further comprising a tubular flexible sheath disposed over said braid and bladder outside said helix and attached at a proximal end thereof to said anchor and rotatably at a distal end thereof to said swivel means.

8. The elongated flexible probe of claim 7 wherein said swivel means has an outer bushing to which said sheath is affixed, and an inner portion which is rotatably supported in said bushing and which supports a proximal end of said bending neck.

9. The elongated probe of claim 8 further comprising a viewing head supported at a distal end of said bending neck, a signal conduit coupled to said viewing head and extending within said bending neck, through a passage in said swivel member, axially within the helical biased torsional fluid dynamic motor, through a passage in said anchor, and proximally through said insertion tube to a viewing device; and a tube over said conduit extending from said swivel member proximally within and radially inward of the helical fluid dynamic motor, and through the passage in said anchor and into the insertion tube and coupled to a controlled fluid pressure source to control the bending of said bending neck.

10. The elongated flexible probe of claim 9 wherein said fluid conduit means of said anchor includes an additional tube extending from said anchor to an additional controlled fluid pressure source to control the rotation of said helical fluid dynamic motor.

11. The elongated flexible probe of claim 10 wherein said additional tube communicates with the interior of the insertion tube, which communicates with said additional pressure source.

12. The elongated probe of claim 9 wherein said tube is loosely fitted in said anchor passage to permit relative rotation of said tube and said anchor.

* * * * *